(12) United States Patent
Meisberger et al.

(10) Patent No.: US 10,111,992 B2
(45) Date of Patent: Oct. 30, 2018

(54) APPARATUS AND METHOD FOR DETERMINING THE LIQUID LEVEL OF SALVAGED BLOOD IN A BLOOD COLLECTION RESERVOIR OF AN AUTOLOGOUS BLOOD TRANSFUSION SYSTEM

(71) Applicant: Fresenius Kabi Deutschland GmbH, Bad Homburg (DE)

(72) Inventors: Artur Meisberger, St. Wendel (DE); Melanie Fahrendorff, Niederkassel (DE); Manfred Eirich, Freiensteinau (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/112,926

(22) PCT Filed: Dec. 17, 2014

(86) PCT No.: PCT/EP2014/078124
§ 371 (c)(1),
(2) Date: Jul. 20, 2016

(87) PCT Pub. No.: WO2015/124235
PCT Pub. Date: Aug. 27, 2015

(65) Prior Publication Data
US 2016/0375185 A1    Dec. 29, 2016

(30) Foreign Application Priority Data
Feb. 24, 2014    (EP) .................................... 14156384

(51) Int. Cl.
*A61M 1/02*    (2006.01)
*A61M 1/36*    (2006.01)
*G01F 23/292*    (2006.01)

(52) U.S. Cl.
CPC ........ *A61M 1/0259* (2013.01); *A61M 1/3627* (2013.01); *G01F 23/2924* (2013.01);
(Continued)

(58) Field of Classification Search
CPC .............. A61M 1/0259; A61M 1/3627; A61M 2205/18; A61M 2205/3306;
(Continued)

(56) References Cited

U.S. PATENT DOCUMENTS 3,851,181 A    11/1974 Heule
4,193,004 A    3/1980 Lobdell et al.
(Continued)

FOREIGN PATENT DOCUMENTS

DE    10 039 765 A1    2/2002
EP    0 777 111 A1    6/1997
(Continued)

OTHER PUBLICATIONS

International Search Report and Written Opinion, counterpart PCT Appl. No. PCT/EP2014/078124 (dated Mar. 5, 2015).

*Primary Examiner* — David Porta
*Assistant Examiner* — Blake Riddick
(74) *Attorney, Agent, or Firm* — Cook Alex Ltd.

(57) ABSTRACT

Disclosed is an apparatus and method for determining the liquid level of salvaged blood in a blood collection reservoir (11) of an autologous blood transfusion system (20), comprising sensing means (10, 12) for periodically sensing the liquid level of the salvaged blood in said blood collection reservoir (11) and outputting corresponding signals, and determining means (2) for determining the liquid level of the salvaged blood in said blood collection reservoir (11) based on said output signal of said sensing means. The sensing means comprises a plurality of light emitters (12) disposed on a first side of said blood collection reservoir (11) at
(Continued)

different height levels (L1-L9) for emitting light and a plurality of light receivers (10) disposed at said different height levels (L1-L9) on a second side of said blood collection reservoir (11) opposite to said first side for sensing light emitted by said light emitters (12) and transmitted through said blood collection reservoir (11). Parameters of the optical set-up used for detection and signal analysis may be adjusted individually and dynamically so that disturbing effects caused e.g. by absorptive films on the inner surface of the blood collection reservoir (11) may be identified and prevented to thereby enhance the reliability of signal detection and analysis.

18 Claims, 4 Drawing Sheets

(52) U.S. Cl.
CPC . *A61M 2205/18* (2013.01); *A61M 2205/3306* (2013.01); *A61M 2205/3313* (2013.01); *A61M 2205/3389* (2013.01); *A61M 2205/52* (2013.01)

(58) Field of Classification Search
CPC .. A61M 2205/3313; A61M 2205/3389; A61M 2205/52; G01F 23/2924
USPC ............... 250/341.7, 338.1, 341.1, 343, 345
See application file for complete search history.

(56) References Cited

U.S. PATENT DOCUMENTS

| | | | | |
|---|---|---|---|---|
| 4,275,726 | A | | 6/1981 | Schael |
| 4,680,475 | A | | 7/1987 | Tansony et al. |
| 4,834,743 | A | * | 5/1989 | Valerio ............... A61M 1/02 604/403 |
| 4,919,817 | A | * | 4/1990 | Schoendorfer ......... A61M 1/34 210/321.68 |
| 4,976,682 | A | * | 12/1990 | Lane ................ A61M 1/0031 604/6.07 |
| 5,055,198 | A | * | 10/1991 | Shettigar ............. A61M 1/02 210/104 |
| 5,141,486 | A | * | 8/1992 | Antwiler ............ A61M 1/3693 494/27 |
| 5,215,519 | A | * | 6/1993 | Shettigar ................ A61M 1/02 422/44 |
| 5,407,425 | A | * | 4/1995 | Werner ................ A61M 1/3621 604/6.07 |
| 5,437,598 | A | * | 8/1995 | Antwiler ............. A61M 1/3693 494/1 |
| 5,441,482 | A | * | 8/1995 | Clague ................ A61M 1/0058 261/79.2 |
| 5,458,566 | A | * | 10/1995 | Herrig ................ A61M 1/3624 128/DIG. 13 |
| 5,658,271 | A | * | 8/1997 | Loubser ............. A61M 1/0209 604/409 |
| 5,665,061 | A | | 9/1997 | Antwiler |
| 5,876,611 | A | * | 3/1999 | Shettigar ............. A61M 1/3621 210/103 |
| 5,919,125 | A | * | 7/1999 | Berch .................. B04B 5/0442 494/41 |
| 5,976,388 | A | * | 11/1999 | Carson ............... A61M 1/0281 210/194 |
| 6,251,295 | B1 | * | 6/2001 | Johnson ............. A61M 1/3621 210/650 |
| 6,964,646 | B1 | * | 11/2005 | Biesel ................ A61M 1/3633 210/252 |
| 7,710,567 | B1 | | 5/2010 | Mentzer et al. |
| 2002/0085952 | A1 | * | 7/2002 | Ellingboe ........... A61M 1/3621 422/45 |
| 2003/0195452 | A1 | * | 10/2003 | Hunley ................ A61M 1/367 604/4.01 |
| 2004/0243105 | A1 | * | 12/2004 | Swan .................. A61M 1/0013 604/543 |
| 2006/0058167 | A1 | * | 3/2006 | Ragusa .............. A61M 1/3693 494/5 |
| 2006/0226057 | A1 | * | 10/2006 | Robinson ........... A61M 1/3693 210/103 |
| 2008/0108931 | A1 | * | 5/2008 | Bobroff ............... A61M 1/0209 604/6.01 |
| 2009/0050827 | A1 | * | 2/2009 | Takahashi ............ F16C 19/386 250/577 |
| 2009/0314724 | A1 | * | 12/2009 | Nierich ............... A61M 1/0281 210/797 |
| 2012/0078137 | A1 | * | 3/2012 | Mendels ................ A61B 5/205 600/584 |
| 2013/0026084 | A1 | | 1/2013 | Schneider et al. |

FOREIGN PATENT DOCUMENTS

| | | |
|---|---|---|
| WO | WO 2010/141458 A2 | 12/2010 |
| WO | WO2011/095573 | 8/2011 |

* cited by examiner

APPARATUS AND METHOD FOR DETERMINING THE LIQUID LEVEL OF SALVAGED BLOOD IN A BLOOD COLLECTION RESERVOIR OF AN AUTOLOGOUS BLOOD TRANSFUSION SYSTEM

The present application is a U.S. National Stage of PCT International Patent Application No. PCT/EP20141078124, filed Dec. 17, 2014, which claims priority to EP Application No. 14156384.1, filed Feb. 24, 2014, both of which are hereby incorporated herein by reference.

FIELD OF INVENTION

The present invention relates in general to an autologous blood transfusion system and method for the recovery and washing of salvaged blood collected from a surgical site of a patient and relates particularly to an enhanced method for determining the liquid level of the salvaged blood in a blood collection reservoir of an autologous blood transfusion system.

BACKGROUND OF INVENTION

Autologous blood transfusion systems (autotransfusion devices) are widely used for the recovery and washing of salvaged blood collected from a patient particularly at a surgical site, where a large volume blood loss can be expected—e.g. aneurysm, total joint replacement, and spinal surgeries. In such systems the salvaged blood is temporarily stored in a blood collection reservoir for re-use. A reliable determination of the liquid level or volume of the salvaged blood in the blood collection reservoir is crucial for surgeries. Inter alia it is important to avoid a complete depletion of the blood collection reservoir. Furthermore, a reliable process control in such systems requires exact information on the liquid level or volume of the salvaged blood in the blood collection reservoir.

For this purpose often the weight of the blood collection reservoir is monitored by means of a controller and upon reaching predetermined or pre-calibrated threshold values the controller outputs signals for further process control.

An example for such an approach is disclosed in U.S. Pat. No. 5,458,566, wherein the weight of the blood collection reservoir is monitored using a strain gage device to compute the volume of fluid present in the reservoir. When it is determined that a sufficient volume of fluid is present in the reservoir, the system initiates a new FILL cycle. The washing method of this autotransfusion device is not continuous but discontinuous. Thus, the response time of the volume measurement can be slower. The blood collection reservoir is supported vertically by a radially inner support member and is subject to vertical forces during system operation. The device further comprises a radially outer support member secured to a mounting surface. The strain gage is coupled between the inner support member and outer support member for sensing vertical strain forces therebetween and converting vertical forces originating with the tubes into horizontal forces. Around the blood collection reservoir many different conduits are arranged, to which personnel at the surgical site must have free and quick access e.g. for security reasons. This somehow contradicts the requirements of a smooth and steady environment required by the strain gage device itself. Thus, it is difficult to ensure a robust and reliable determination of the liquid level or volume of salvaged blood in the blood collection reservoir.

EP 2531823 A1 of the applicant discloses a method and apparatus for the capacitive level measurement of a liquid medium in a bubble trap of a dialysis machine.

U.S. Pat. No. 4,275,726 of the applicant discloses an apparatus and method for balancing the fluids withdrawn from a patient and the fluids simultaneously returned into the patient for use in exchange blood transfusion, infusion therapy in conjunction with forced diuresis or haemofiltration. In this approach the liquid level of a liquid reservoir used for temporarily storing a liquid is sensed by means of a row of radiation emitters and a row of radiation receivers disposed on a side of the liquid reservoir opposite to the radiation emitters, which generate an output signal representative of the transmission at the various different height levels of the collection reservoir. Use of this method for autotransfusion devices is not disclosed. Furthermore, problems caused by obstruction of the light beams transmitted through the reservoir caused e.g. by a blood or lipid film on the inner surface of the reservoir are not handled.

Thus, there exists a need for more robust and reliable concepts for determining the liquid level of salvaged blood in a blood collection reservoir of autologous blood transfusion systems (autotransfusion devices).

SUMMARY OF INVENTION

It is an object of the present invention to provide an enhanced autologous blood transfusion system and method using a robust and reliable apparatus and method for determining the liquid level of salvaged blood in a blood collection reservoir of such an autologous blood transfusion system. It is a further object of the present invention to provide a computer program product for use in such an autologous blood transfusion system for determining the liquid level of salvaged blood in a blood collection reservoir.

This problem is solved by an autologous blood transfusion system according to claim 1, by a method for determining the liquid level of salvaged blood in a blood collection reservoir of such an autologous blood transfusion system as claimed by claim 8 and by a computer program product as claimed by claim 15. Further advantageous embodiments are the subject-matter of the dependent claims.

According to the present invention there is provided an autologous blood transfusion system for the recovery and washing of salvaged blood collected from a surgical site of a patient, comprising a blood collection reservoir for storing the collected blood, an optical detection setup for periodically detecting the liquid level of the salvaged blood in said blood collection reservoir optically, particularly by means of measuring the transmission of light beams, particularly of pulsed light beams, passing through the blood collection reservoir and outputting a signal in correspondence to signals detected by said optical detection setup, and a processor for determining the liquid level of the salvaged blood in said blood collection reservoir based on said output signal of said sensing means, said optical detection setup comprising a plurality of light emitters disposed on a first side of said blood collection reservoir at different height levels for emitting light and a plurality of light receivers disposed on a second side of said blood collection reservoir opposite to said first side for sensing light emitted by said light emitters and transmitted through said blood collection reservoir and for outputting said output signal.

Use of an optical detection set-up enables a more robust and reliable determination of the liquid level of salvaged blood in a blood collection reservoir. In particular, no mechanical elements, coupling members or sensors are required. Furthermore, the optical set-up enables a fully opto-electronic signal detection and a fully electronic signal analysis, which offers additional advantages, such as simple but reliable variation of the measurement conditions and parameters used for signal analysis.

Preferably, the light emitters and light sensors are disposed at regular spacings along the vertical direction of the blood collection reservoir and are distributed over the entire height of the blood collection reservoir. According to further embodiments, however, the light emitters and light sensors may also be disposed at a given higher density in regions that are considered to be of particular importance for assessment of the process conditions in the blood collection reservoir or for a precise signal analysis. The light receivers (sensors) are disposed spaced apart from each other and may be disposed at the same different height levels as the light emitters.

According to a further embodiment the light emitters are pulsed light emitters for emitting light pulses, preferably infrared light pulses, particularly short light pulses of a duration of e.g. 50 µsec, so that the amount of energy, which is deposited in the salvaged blood, can be reduced significantly. Furthermore, the measurement can be performed periodically at frequencies that are significantly different to those of noise sources, such as mains current, fluorescent tubes or other kinds of light sources typically used at surgery sites. Furthermore, the processor is configured for switching the light emitters on and off individually in correspondence to a control signal, which switches on and off the light emitters, and said processor is further configured for analyzing signals output by light receivers that correspond to the light emitters individually and in correspondence with such a control signal. Thus, the conditions can be determined more reliable as a function of the vertical height level along the blood collection reservoir.

According to a further embodiment the processor is configured for a) reading output signals of said light receivers sequentially along a vertical direction of said blood collection reservoir, b) comparing said output signals with a predetermined threshold value, and c) determining the liquid level of the salvaged blood in said blood collection reservoir based on said comparing said output signals with said predetermined threshold value. The threshold value enables a reliable discrimination of transmission changes in the sequence of output signals read-out from the plurality of light receivers and can be varied and re-adjusted easily, so that the method can be used for various different process conditions.

According to a further embodiment the processor is configured for individually adjusting detection parameters associated with the plurality of light emitters and the plurality of light receivers. As will be shown in the following, this enables to suppress the disturbing effects particularly of absorptive films of contaminants, such as fat or clotted blood, on the inner surface of the blood collection reservoir, which otherwise could result in wrong or even misleading information. According to the present invention these detection parameters include at least one of an output power of the light emitters, a gain of an amplifier used for amplifying output signals output by the plurality of light receivers and a threshold value used by the determining means for analyzing the output signals output by the plurality of light receivers.

According to a further embodiment the processor is further configured for a) identifying a conspicuous signal out of said output signals of said light receivers based on a comparison of the output signals of at least two light receivers out of said plurality of light receivers (which may be directly adjacent light receivers), b) varying a detection parameter of a light emitter and/or of a light receiver and/or of an amplifier associated with said conspicuous signal, and c) repeating said step of determining the liquid level of the salvaged blood in said blood collection reservoir using said varied detection parameter. In the sense of the present application a conspicuous signal is a signal that indicates abnormal transmission changes between output signals of at least two (preferably at least three) directly adjacent light receivers or sequences of at least two (preferably at least three) transmission values that might be caused by blood or lipid films on the inner surface of the storage vessel or similar effects locally perturbing the optical transmission through the storage vessel.

According to a further embodiment the processor is further configured for determining the liquid level of the salvaged blood in said blood collection reservoir using said varied detection parameter if a signal of a light receiver or amplifier associated with said varied detection parameter is not identified as a conspicuous signal in said identifying step when repeating said step of sensing the liquid level of the salvaged blood in said blood collection reservoir using said varied detection parameter.

According to a further embodiment the processor further comprises a look-up-table for determining conditions of the collected blood collected in the blood collection reservoir based on a comparison of the respective output signal with contents of the look-up-table. The contents of the look-up-table may particularly reflect the typical transmission (or absorption) characteristics of typical process conditions or contaminants that might occur in the blood collection reservoir, and might be knowledge-based or result from an initial calibration or training method performed prior to the measurement method. As an example: if the output signals outputted by a series of light receivers are in accordance with a typical transmission expected to occur below the filling level, i.e. within the salvaged blood stored in the storage vessel of the system, and if the signal outputted by an intermediate light receiver of said series of light receivers indicates an exceptionally higher or lower transmission that would otherwise indicate air or a rather thick blood at the height level of the corresponding light receiver in the storage vessel, the output signal of this intermediate light received is considered as a conspicuous signal, indicating an abnormal or unusual transmission change at the height level of the intermediate light receiver that requires a specially dedicated measuring procedure at this height level for further discriminating the reason for this abnormal or unusual transmission change at the height level of the intermediate light receiver.

According to a further embodiment the processor is further configured for starting or controlling the washing process based on said filling level, particularly upon reaching preset filling levels in the storage vessel, or for generating a warning message and outputting said warning message via an interface, if the filing level measured indicates a complete or nearly complete depletion of the storage vessel.

A further aspect of the present invention relates to a corresponding method for determining the liquid level of salvaged blood in a blood collection reservoir of such an autologous blood transfusion system as described in the following.

A further aspect of the present invention relates to a corresponding computer program product for determining the liquid level of salvaged blood in a blood collection reservoir of such an autologous blood transfusion system as described in the following.

BRIEF OVERVIEW ON DRAWINGS

Hereinafter the invention will be described with reference to exemplary embodiments and referring to the enclosed drawings, wherein.

Throughout the drawings, identical reference numerals designate identical or substantially equivalent elements or groups of elements

DETAILED DESCRIPTION OF PREFERRED EMBODIMENTS

Figure 4:
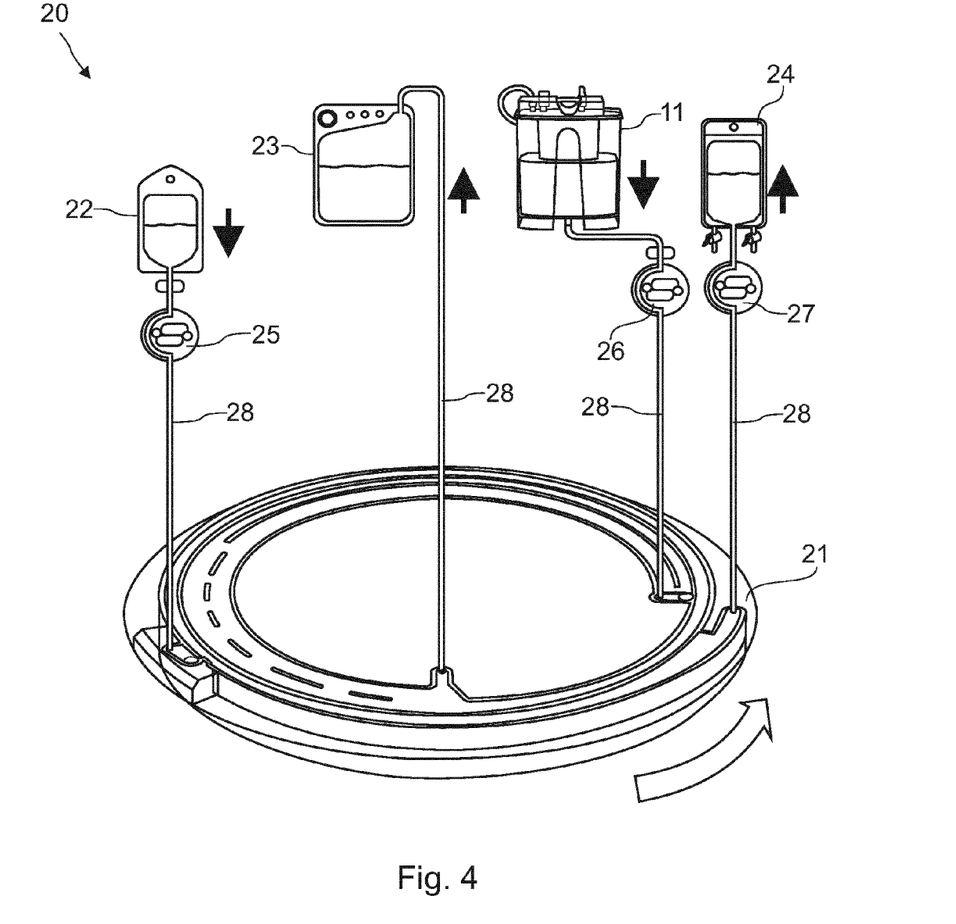
FIG. 4 schematically shows a washing chamber of an autologous blood transfusion system comprising a blood collection reservoir, wherein the liquid level of the salvaged blood in the blood collection reservoir is determined in accordance with the present invention.

Before describing a method for determining the liquid level of salvaged blood in a blood collection reservoir of an autologous blood transfusion system according to the present invention, in the following the general environment of utilizing such a method in an autologous blood transfusion system or autotransfusion device will be described briefly with reference to FIG. 4, which shows a washing chamber of such an autologous blood transfusion system using a continuous flow technique for washing blood.

More specifically salvaged blood that has been e.g. collected from a surgical site of a patient, enters a continuous washing process in which red blood cells are resuspended with a saline solution and blood plasma and other contaminants are removed. The salvaged blood is pumped by pump 28 from the reservoir for collected blood 11 via conduit 28 to enter the washing process together with a washing solution pumped by pump 28 from reservoir 22 via conduit 28. In this process blood is concentrated to a haematocrit (HCT) of e.g. approx. 80% and most of the blood plasma, cellular debris, white blood cells, platelets, anticoagulant and other unwanted constituents are separated out. Furthermore, a removal of non-emulsified fat as complete as possible is performed. Red cells from a red cell concentrate stored in reservoir 24 are packed to a HCT concentration of e.g. 60-65%. The recovered blood is then infused into the patient's body at a different site (not shown).

The blood collection reservoir 11 in this process is a transparent storage vessel and may be a standard reservoir utilizing a special double lumen suction tubing, wherein fluid is aspirated from the operative field and is mixed with an anticoagulant solution. Collected fluid is filtered in a sterile cardiotomy reservoir. The reservoir contains a filter and has a capacity of between two and three liters of fluid. The blood collection reservoir 11 may have a conical funnel-shaped bottom.

Figure 1:
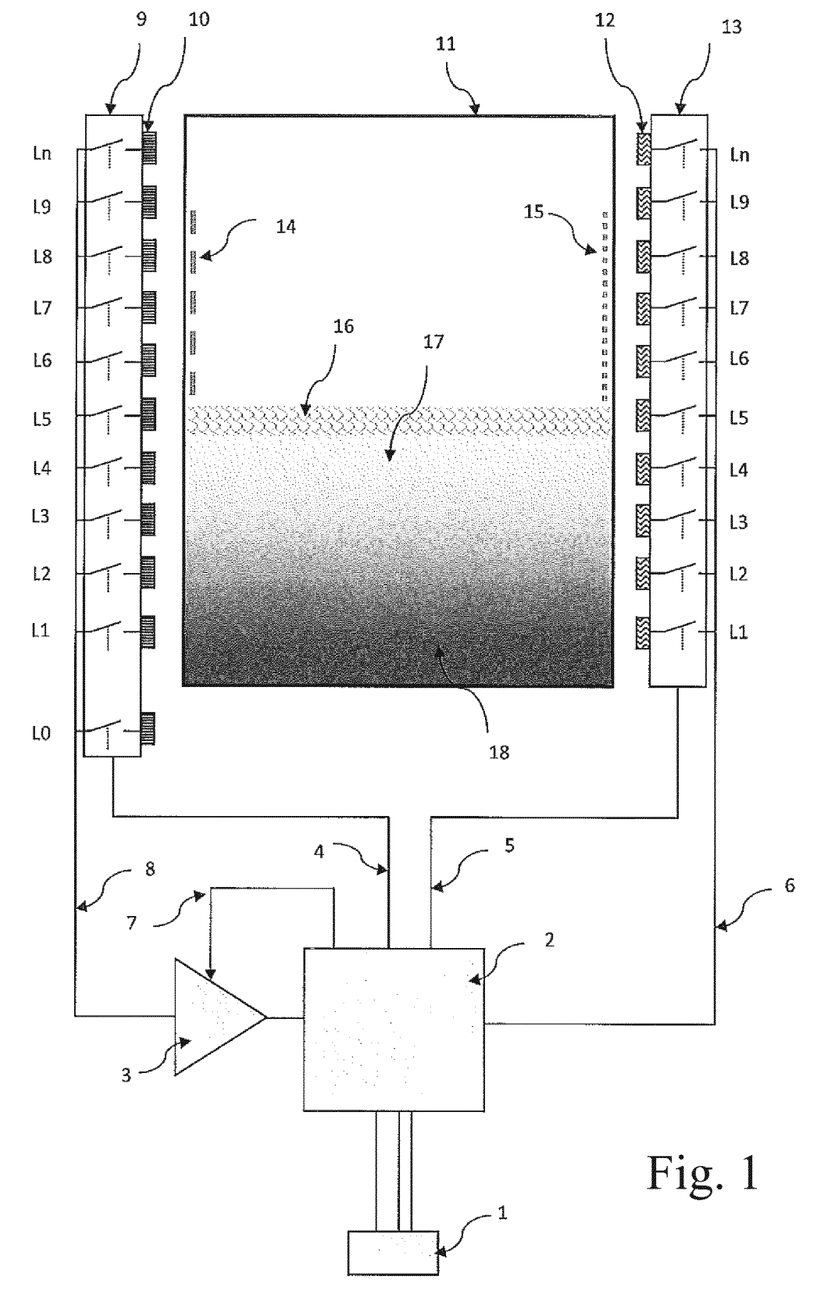
FIG. 1 schematically shows an apparatus for determining the liquid level of salvaged blood in a blood collection reservoir of an autologous blood transfusion system according to the present invention.

FIG. 1 shows a setup for determining the liquid level or volume of salvaged blood in the blood collection reservoir 11 used in an autologous blood transfusion system as described above with reference to FIG. 4. The storage vessel 11 is filled with salvaged blood together with a washing solution. The longer the washing process is employed in the above washing process, the more the volume in the reservoir 11 separates into the following regions: salvaged blood having a high HCT 18, particularly with sedimentation at the bottom of storage vessel 11, salvaged blood having a low HCT 17, with HCT values even close to a clear plasma solution, and a layer of foam 16 on top of the surface of the salvaged blood. The layer of foam 16 may have a thickness of up to 1-2 centimeters. During the washing process the filling level of the salvaged blood in the storage vessel 11 repeatedly moves upwards and downwards. When moving upwards and downwards, portions with films of e.g. clotted blood 14 or lipid 15 may remain locally on the inner surface of the storage vessel 11.

For measuring the filling level (volume) of the salvaged blood in the storage vessel 11, the transmission of light through the storage vessel 11 is measured by means of an optical setup. More specifically, a plurality of light emitters 12, such as light-emitting diodes (LEDs), are disposed on a first side of storage vessel 11 at different height levels indicated by reference numerals L1-L9, which emit light beams preferably in the infrared wavelength range to reduce deposition of radiation energy in the salvaged blood. The transmitted light intensity is measured by a plurality of light receivers 10, such as photodiodes, disposed on a side of the storage vessel 11 opposite to the light emitters 12. Hereinafter, in order to identify the light receivers 10 and light emitters 12, respectively, at the respective height levels L1, L2, . . . Ln, these light receivers and light emitters are named 10.1, 10.2, . . . 10.$n$ and 12.1, 12.2, . . . 12.$n$, respectively. The light emitters 12 and light receivers 10 may be disposed in a protective housing that may be sleeved onto the storage vessel 11, which is usually a disposable, and is configured for re-use. The light emitters 12 and light receivers 10 may be disposed at the same height levels L1-L9.

An array of electronic switches 13 is associated with the light emitters 12 so that the light emitters can be switched on and off individually by means of control signals of controller 2 transmitted via transmission line 5. A further array of electronic switches 9 is associated with the light receivers 10 so that the transmission signals output by the light receivers 10 can be read-out individually via transmission line 4. The read-out transmission signals are amplified by an amplifier 3 using a gain factor that can be adjusted by the controller 2 via control line 7. More specifically, the transmission signals output by different light receivers 10.1, . . . 10.$n$ can be amplified individually by means of gain factors individually adjusted for each of the light receivers 10.1, . . . 10.$n$.

For determining the filling level or volume of salvaged blood in the storage vessel 11, the output signals of the light receivers 10.1, . . . 10.$n$ are analyzed for determining a transition from a relatively low transmission (indicating a certain absorption of light by salvaged blood) to a relatively high transmission (indicating no absorption of light by salvaged blood). More specifically, the output signals of the light receivers 10.1, . . . 10.$n$ are read-out sequentially along a vertical direction of the storage vessel, e.g. in the order starting with the lowest sensor L.1 to the uppermost sensor L.n or in the opposite order, and a transition from relatively low transmission to relatively high transmission is determined, i.e. where a transition from dark regions to less absorptive regions occurs, which corresponds to the actual filling level in the storage vessel 11 or e.g. to the transition from salvaged blood to saline solution. For this purpose, algorithms may be used which use a threshold value for discriminating between signals indicating a relatively low transmission and signals a relatively high transmission. According to a first embodiment the light beams emitted by the light emitters 12 are collimated light beams or nearly collimated light beams having a small beam divergence. Thus, the light receivers 10 disposed on a side of the storage vessel 11 opposite to said light emitters 12 may be disposed at the same height levels L1-L9 as the light emitters 12 and may detect only of one light beam transmitted through the storage vessel 11 and emitted by the directly opposite light emitter. According to a preferred second embodiment, however, the light emitters 12 emit highly divergent light beams, e.g. of a divergence angle of 120°, in which case the light receivers 10 on the opposite side of the storage vessel 11 may detect the light beams emitted by several light emitters 12. More specifically, the light receivers 12 disposed in the central part of the storage vessel, such as light receivers 12 disposed at height levels L5 or L6, may detect the light beams emitted by two or even more of the directly opposite light emitters, such as light emitters 12 disposed at height levels L4-L6 (for the light receiver disposed at height level L5) and light emitters 12 disposed at height levels L5-L7 (for the light receiver disposed at height level L6). As will be shown in the following, according to the present invention the relatively high divergence angle of the light beams emitted by the light emitters may further assist to more easily and reliably discriminate conspicuous signals caused particularly by blood or lipid films on the inner surface of the storage vessel 11, which result in locally abnormal transmission changes.

Based on the above information the washing process may be started or performed e.g. upon reaching preset filling levels in the storage vessel 11 or at filing levels without saline solution supernatant. The bottom light receiver (at height level L1) or a bottom light receiver (at height level L0) are used for indicating a complete depletion of the storage vessel 11, in which case a warning message is generated by controller 2 and outputted via interface 1 to external devices, such as displays, alarm devices or the like. For this purpose, it may be of advantage, if the bottom of the storage vessel 11 is slanted, conically tapered and the bottom light receiver 10 at height level L0 measures the transmission in the region of the slanted, conically tapered bottom of the storage vessel 11.

More specifically, the washing process may be started only if a predetermined minimum filling level is initially provided in the storage vessel 11, which may correspond to a liquid volume of e.g. 0.75 l or 1 l. By means of the measured filling level the washing process is controlled such that a minimum filling level of e.g. 50 ml in the storage vessel 11 is ensured during the whole process or surgery and that a complete depletion of the storage vessel 11 is always prevented, e.g. in order to avoid the presence of air or foam in centrifuge used in the washing process or at the locations of sensors, which might otherwise give rise to wrong or misleading signals. Thus, the washing process may be interrupted temporarily, if a nearly complete depletion of the storage vessel 11 is determined based on the sensed filling level, e.g. if only the bottom light receiver 10 at height level L0 indicates a filling level but none of the other light receivers 10 at the other height levels L1-L9. As a result of such a temporary interruption of the washing process the filling level in the storage vessel 11 will rise again due to the collecting of additional salvaged blood from the patient at the surgical site, until a predetermined upper filling level is reached again finally, e.g. corresponding to a volume of 0.75 l or 1 l, which triggers again the washing process. The above loop may be repeated until a user, particularly an anesthetist, inputs a signal to controller 2 via interface 1 that the washing process shall be terminated, e.g. if it has been decided that the surgery will be terminated shortly.

Figure 2:
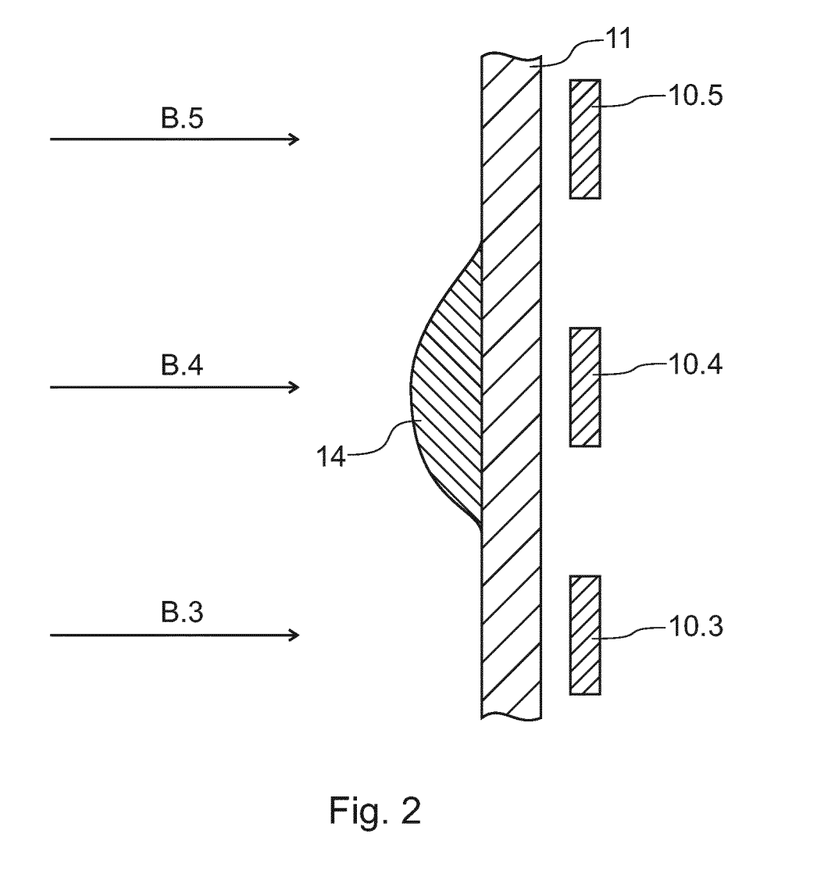
FIG. 2 is a partial cross-sectional view of an inner wall portion of the blood collection reservoir of FIG. 1 with a contamination caused by a blood or lipid film on the inner surface of the blood collection reservoir.

FIG. 2 is a partial cross-sectional view of a wall portion of the storage vessel 11 of FIG. 1 with a contamination caused by blood or lipid films 14, 15 on the inner surface of the storage vessel 11. These blood or lipid films 14, 15 result in a locally reduced transmission of the sensing light emitted by the light emitters 12, which is independent of the transmission (absorption) of the content of the storage vessel at given height level. These blood or lipid films 14, 15 are independent of the actual filling level in the storage vessel 11 and may remain on the inner surface even above the actual filling level, if the filling level of salvaged blood shrinks to a lower height level, as shown in FIG. 1. A repeated movement of the surface of the salvaged blood upwards and downwards during the washing process, even results in the agglomeration of such blood or lipid films 14, 15 on the inner surface of the storage vessel 11. As shown in FIG. 2, the presence of blood film 14 at the height level L4 of light receiver 10.4 results in a reduced transmission of the sensing light beam B.4 as compared to the transmission of the sensing light beams B.3 and B.5 at the height levels L3 and L5, respectively. This results in measurement of an incorrect transmission ratio at height level L4, which can cause a wrong or even misleading discrimination (determination) of the actual filling level in the storage vessel 11 or of the transition from salvaged blood to saline solution inside the storage vessel 11, which is to be prevented.

According to the present invention the sequential reading-out of the transmission signals from the light receivers 10 along the vertical direction of the storage vessel 11 may be used to identify conspicuous signals at height levels, which are not in accordance with standard transmission profiles in the storage vessel to be expected under normal operating conditions and which otherwise might result in a wrong or even misleading discrimination of the actual filling level in the storage vessel 11 or of the transition from salvaged blood to saline solution inside the storage vessel 11. It should be noted that such standard transmission profiles in the storage vessel to be expected under normal operating conditions may be stored in a look-up table If one assumes e.g. for the state shown in FIG. 2 that light receivers 10.3-10.5 are above the actual filling level in the storage vessel 11, then the signals of light receivers 10.3 and 10.5 will indicate a relatively high transmission that might even correspond to a transmission of 100% (if one takes into account reflection losses at the various interfaces), whereas the signal of light receiver 10.4 will indicate a relatively low transmission. Under normal conditions in the storage vessel 11 such a sequence of transmission values at height levels L3-L5 cannot be the result of normal transmission changes near the actual liquid surface in the storage vessel 11. Rather, the controller 2 will assume that the signal corresponding to light beam BA is a conspicuous signal and that no transition region exists at these height levels, as outlined in the following. In the sense of the present application conspicuous signals are signals that indicate abnormal transmission changes between signals of at least two (preferably at least three) directly adjacent light receivers 12 or sequences of at least two (preferably at least three) transmission values that might be caused by blood or lipid films on the inner surface of the storage vessel 11 or similar effects locally perturbing the optical transmission through the storage vessel 11.

As another example, if one assumes e.g. for the state shown in FIG. 2 that light receivers 10.3-10.5 are below the actual filling level in the storage vessel 11, then the signals of light receivers 10.3 and 10.5 will indicate a transmission typical for salvaged blood, which is already relatively low, whereas the signal of light receiver 10.4 will indicate an even lower transmission that might even be zero and is caused by the additional presence of blood film 14 at the height level L4 corresponding to light receiver 10.4. Under normal conditions in the storage vessel 11 such a sequence of transmission values at height levels L3-L5 cannot be the result of transmission changes near the actual liquid surface in the storage vessel 11. Rather, the controller 2 will assume for such a measured signal that the signal corresponding to light beam B.4 is a conspicuous signal and that no transition region exists at these height levels, as outlined in the following, and will consider the transmission measured at height level L4 as a conspicuous transmission.

In order to discriminate a conspicuous signal at height level L4 caused by a zero or abnormally low (conspicuous) transmission, the following approach may be pursued.

For this purpose, in the following it is assumed that usually the transmission values at the different height levels L3-L5 in FIG. 2 are measured by means of individual light beams B.3-B.5 that are selectively turned on for measuring the transmission at a given height level. More specifically, light beam B.3 at height level L3 is used for measuring the transmission by means of associated light receiver 10.3, light beam B.4 at height level L4 is used for measuring the transmission by means of associated light receiver 10.4 and light beam B.5 at height level L5 is used for measuring the transmission by means of associated light receiver 10.5. If a zero transmission or conspicuously low transmission is measured at height level L4, the measurement of the transmission is repeated with all light beams B.3-B.5 turned on. As the light beams B.3-B.5 have a relatively high divergence angle (of e.g. 120°), a certain percentage of the power of adjacent light beams B.4 and B.6 will propagate to light receiver 10.4 at height level L4. Thus, the total light power available at height level L4 for measuring the transmission at this height level is temporarily increased, which also holds for the total light powers available at the neighboring height levels. At the increased light power the transmission measured at height level L4 might not be zero but non-vanishing. A comparison with the transmission values measured at the neighboring height levels L3 and L5 and analyzing the transmission values finally results in information, whether the conspicuous signal at height level L4 previously measured is the result of a film on the inner surface of the storage vessel 11 or not. For future measurements of the transmission at height level L4 the higher power for beam L4 may be used.

As will become apparent to a person skilled in the art, a similar discrimination may also be obtained, if the other parameters relevant for the detection of the light beams (hereinafter detection parameters) are varied, particularly the output power of the light emitters and/or the gain of amplifiers used for amplifying signals output by the respective light receivers and/or a threshold value used by the processor or controller 2 for analyzing the output signals of the light receivers.

As will become apparent to a person skilled in the art, a similar discrimination may also be obtained, if the light beams emitted by the light emitters are not highly divergent light beams but instead collimated or nearly collimated light beams.

As will become apparent to a person skilled in the art, a similar approach, which varies the detection parameters for detecting the transmission at the different height levels individually or collectively, may also be used to discriminate other conditions of the content of the storage vessel, such as the degree of dilution of the salvaged blood contained in the storage vessel 11.

Figure 3:
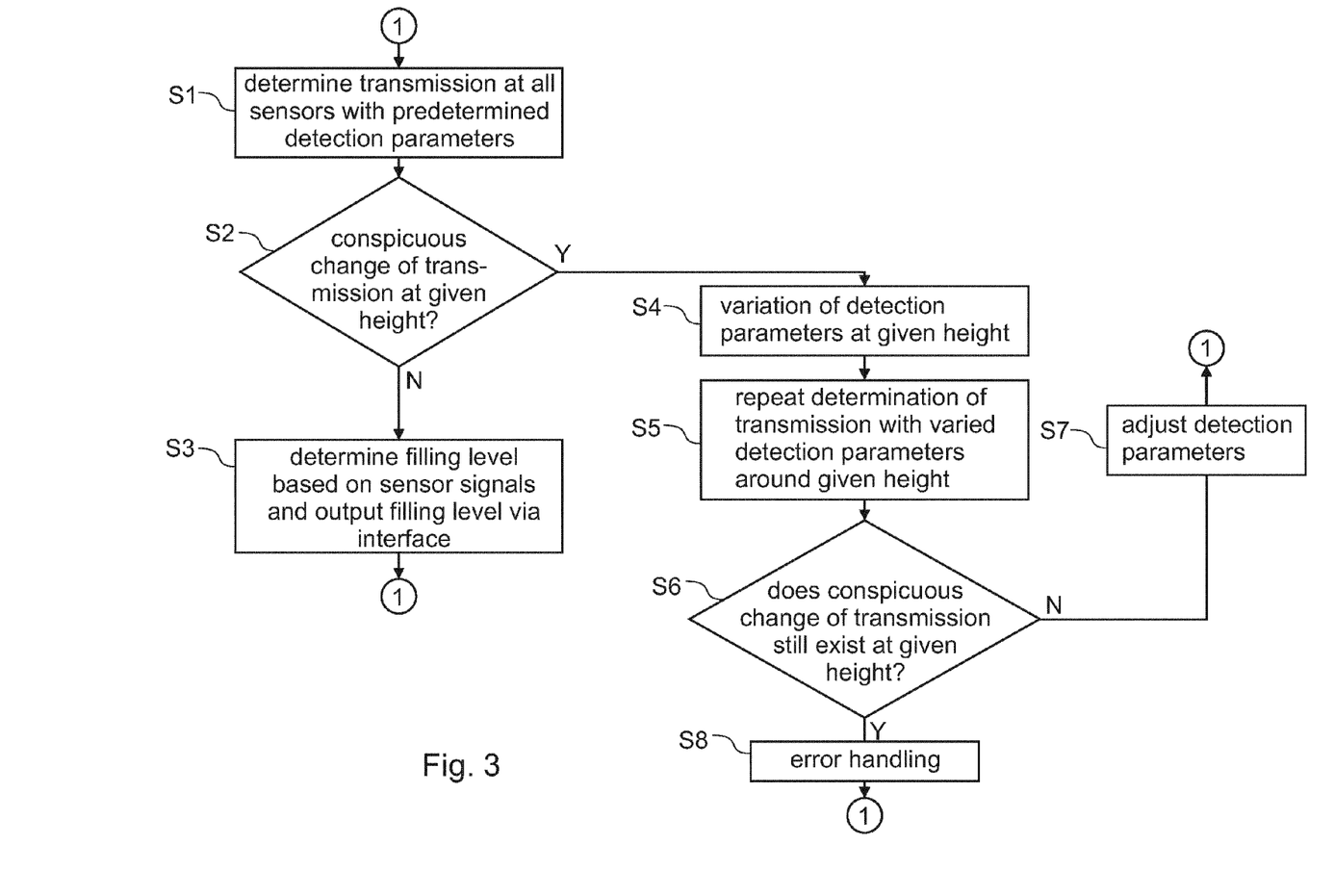
FIG. 3 is a schematic flow diagram of a method for determining the liquid level of salvaged blood in a blood collection reservoir of an autologous blood transfusion system according to the present invention.

FIG. 3 is a schematic flow diagram of a method for determining the liquid level of salvaged blood in a storage vessel of an autologous blood transfusion system (autotransfusion device) according to the present invention, which preferably uses a continuous washing process. For sensing the transmission signals of the light receivers at height levels L1-Ln, detection parameters are used, which in a first cycle are predetermined, e.g. based on a previous calibration step for calibrating all light receivers at height levels L1-Ln for equal sensitivity. In the sense of the present application, these "detection parameters" may be any of an output power of the light emitters 12, a gain of an amplifier 3 used for amplifying signals output by the light receivers 10 and a threshold value used for analyzing the (amplified) output signals of the light receivers 10 in the controller 2, or any other suitable parameter relevant for signal detection and analysis. According to the present invention, these detection parameters are not fixed values but may be adjusted individually for the light receivers L1-Ln and may be adjusted even dynamically while performing the washing process, as will be described in the following.

Referring to FIGS. 1 and 3, in step S1 the transmission at the height levels L1-Ln of light receivers 10 is detected and further analyzed by controller 2 utilizing predetermined detection parameters. For this purpose the signals of the light receivers 10 at height levels L1-L9 are preferably read-out in a given order, e.g. sequentially in vertical direction of the storage vessel 11 from bottom to top or top to bottom. Based on this set of transmission values the controller performs a signal analysis in step S2 using suitable algorithms, for identifying the presence and height level (location) of light sensors indicating conspicuous changes of transmission that are candidates for a wrong or even misleading discrimination of the actual filling level in the storage vessel 11 or of the transition from salvaged blood to saline solution inside the storage vessel 11. For this purpose the analysis may proceed e.g. as described with reference to FIG. 2 above.

If no such conspicuous changes of transmission or conspicuous signals are determined in step S2, then the method proceeds with step S3, in which the controller 2 considers the measured transmissions at the height levels L1-Ln of light receivers 10 as correct and not-misleading and uses the measured transmissions for determining the actual filling level in the storage vessel 11 or the transition from salvaged blood to saline solution inside the storage vessel 11 for further signal processing.

The loop of steps S1-S3 is performed periodically, to thereby obtain information on the actual filling level in the storage vessel 11 or on the transition from salvaged blood to saline solution inside the storage vessel 11 periodically. For this purpose, the light emitters 12 preferably emit short light pulses, at a repetition rate that is substantially different to the frequency of a mains current, to the operation frequency of fluorescent tubes or other kinds of light sources typically used at surgery sites, or to higher harmonics thereof. Thus, disturbing background noise is suppressed and a higher signal-to-noise ratio can be accomplished. As an example, 100 µs infrared light pulses at a repetition rate of 25 Hz may be used in a method according to the present invention.

On the other hand, if in step S2 the controller 2 determines at least one conspicuous change of transmission based on the transmission values measured using the predetermined detection parameters, then the method proceeds with step S4 for varying the detection parameters and with steps S5 and S6 for repeating the above identification of conspicuous changes of transmission.

In the following, the state shown in FIG. 2 is considered, in which the presence of blood film 14 at the height level L4 of light receiver 10.4 results in a reduced transmission at height level L4 compared to the transmission detected at the height levels L3 and L5, respectively, and it is assumed that the controller 2 identifies height level L4 as a location of a conspicuous change of transmission (conspicuous signal). In such a state, in step S4 the detection parameters at height level L4 are varied and the transmission is measured and analyzed in step S5 using such varied detection parameters.

As a first example, the output power of light emitter 12 at height level L4 is selectively increased and/or the gain of amplifier 3 used for amplifying the signal output by light receiver 10 at height level L4 is increased and/or a threshold value used for analyzing the (amplified) output signal of the light receiver 10 at height level L4 in the controller 2 is selectively adjusted in step S4 and the transmission is measured and analyzed in step S5 using such varied detection parameters. If the controller analyzes a transmission for the varied detection parameters that is a typical transmission of salvaged blood, saline solution, foam or air and such a typical transmission behavior has already been observed in step S1 for the adjacent height levels L3 and L5, respectively, then in step S6 no such conspicuous change of transmission is identified at height level L4. Rather, the method proceeds with step S7 to adjust the detection parameters at height level L4 to the new detection parameters used in step S5 and proceeds again with step S1, in which case in step S2 no such conspicuous change of transmission will be identified anymore at height level L4, but rather the method will proceed with step S3.

As a second example, the output powers of light emitters 12 at height levels L3-L5 are selectively increased and/or the gain factor of amplifier 3 used for amplifying the signals output by light receiver 10 at height levels L3-L5 are selectively increased and/or the threshold values used for analyzing the (amplified) output signals of the light receiver 10 at height levels L3-L5 in the controller 2 are selectively adjusted in step S4 and the transmission is measured and analyzed in step S5 using such varied detection parameters. Using the varied detection parameters a far better signal-to-noise ratio is available for a more reliable determination whether the change in transmission at height level L4 results from an actual transition region in the storage vessel 11 or simply from an undesired film 14 on the inner surface of storage vessel 11. For this purpose, the transmission values at height levels L3-L5 are compared with each other in step S5 and analyzed further.

Thus, in the second example, if the controller analyzes a transmission for the varied detection parameters that is a typical transmission of salvaged blood, saline solution, foam or air and such a typical transmission behavior has already been observed in step S1 for the adjacent height levels L3 and L5, respectively, then in step S6 no such conspicuous change of transmission is identified at height level L4. Rather, the method proceeds with step S7 to adjust the detection parameters at height level L4 to the above varied detection parameters and to readjust the detection parameters at the adjacent height levels L3 and L5, respectively, to those detection parameters used previously in step S1. Then the method proceeds again with step S1, in which case in step S2 no such conspicuous change of transmission will be identified anymore at height level L4, but rather the method will proceed with step S3.

If finally, despite the variation of the detection parameters in step S4, still a conspicuous change of transmission is determined in step S6, an error handling routine S8 may be triggered, which will not be described here in detail, but which may comprise outputting an error signal for indicating an unreliable or error state of the measuring system, triggering a supplemental cleaning procedure for cleaning the inner surface of the storage vessel 11, e.g. by rinsing the inner surfaces with a washing solution, or for stopping operation of the washing procedure and issuing a warning/stop signal to the personnel at the surgical site.

The above loop of steps S1-S7 may be repeated several times, until the controller determines that at least one of the detection parameters runs beyond a predetermined parameter range. Then, the above error handling routine S8 may also be triggered. The process may then return to step S1.

As will become apparent to a person skilled in the art, in case of detection of a conspicuous change of transmission in step S2, the detection parameters may be varied in step S4 and/or the further transmission signal analysis may be performed based on knowledge data or calibration data on the typical transmission characteristics in the presence of the standard types of contaminants and conditions of the salvaged blood during the washing process. Such knowledge data may be stored e.g. in a look-up-table (not shown) to which the controller 2 has access or in a memory coupled to or integrated in controller 2.

By means of varying the detection parameters selectively at different height levels, the filling level (volume) of salvaged blood or the transition from salvaged blood to saline solution inside the storage vessel 11 may be determined reliably even under adverse conditions that otherwise would result in incorrect or even misleading measurements and signal analysis.

The approach of varying the detection parameters selectively at different height levels may also be used for calibrating the optical detection setup shown in FIG. 1. If one assumes that the light beams emitted by light emitters 12 are highly divergent, it is apparent that more light will strike on the central light receives 10 and that less light will strike on those light receivers 10 that are disposed at the upper and lower end of the storage vessel 11, such as the light receivers at height levels Ln and L1, respectively. This may be compensated by increasing the power emitted by the correspondingly opposite light emitters 12, i.e. light emitters 12 disposed at height levels Ln and L1, respectively, or the gain of amplifiers used for amplifying the signals output by the light receivers disposed at height levels Ln and L1, respectively.

As will become apparent to a person skilled in the art, the possibility of selectively varying the detection parameters at height levels according to the present invention even makes it possible to derive additional information about the content of the storage vessel 11 at the height levels, such as an analysis of the HCT at the different height levels, the saline concentration at the different height levels or similar parameters of the salvaged blood.

LIST OF REFERENCE NUMERALS

1 Interface/Power supply
2 Controller/Determining means
3 amplifier
4 transmission line
5 transmission line
6 transmission line
7 control line for adjusting gain of amplifier 8 transmission line
9 array of switches
10 array of light receivers
10.3-10.5 light receivers at height levels L3-L5
11 blood collection reservoir
12 array of light emitters
13 array of switches
14 blood film (in blood collection reservoir)
15 lipid film (in blood collection reservoir)
16 foam (in blood collection reservoir)
17 region with low haematocrit (in blood collection reservoir)
18 region with high haematocrit (in blood collection reservoir)
20 autologous blood transfusion system
21 rotating washing chamber
22 reservoir for washing solution
23 waste bag
24 reservoir for red cell concentrate
25 pump
26 pump
27 pump
28 tubing
L1-Ln height levels
L0 height level of bottom light receiver
B.3-B.5 sensing light beams at height levels L3-L5

The invention claimed is:

1. An autologous blood transfusion system for the recovery and washing of salvaged blood collected from a surgical site of a patient, comprising:
a blood collection reservoir for storing the collected blood,
an optical detection setup for periodically detecting a liquid level of the salvaged blood in said blood collection reservoir and for outputting a corresponding output signal, and
a processor for determining the liquid level of the salvaged blood in said blood collection reservoir based on said output signal of said optical detection setup,
said optical detection setup comprising:
a plurality of light emitters disposed on a first side of said blood collection reservoir at different height levels for emitting light and
a plurality of light receivers disposed on a second side of said blood collection reservoir opposite to said first side for sensing light emitted by said light emitters and transmitted through said blood collection reservoir and for outputting said output signal; and
said processor further configured for:
identifying a conspicuous signal out of said output signals of said light receivers based on a comparison of output signals of at least two light receivers out of said plurality of light receivers, said conspicuous signal associated with an abnormal transmission change between the output signals of the at least two light receivers, the output signal of a first of the at least two light receivers being compared against the output signal of a second of the at least two light receivers and the first and second light receivers being directly adjacent,
varying a detection parameter of a light emitter and/or of a light receiver and/or of an amplifier associated with said conspicuous signal, and
repeating said step of determining the liquid level of the salvaged blood in said blood collection reservoir using said varied detection parameter.

2. The autologous blood transfusion system as claimed in claim 1, wherein said light emitters are pulsed light emitters for emitting light pulses and wherein:
said optical detection setup is configured for switching said light emitters on and off individually in correspondence to a control signal, and
said processor is configured for analyzing output signals outputted by light receivers that correspond to said light emitters individually and in correspondence with said control signal.

3. The autologous blood transfusion system as claimed in claim 1, wherein said processor is configured for:
reading-out output signals of said light receivers sequentially along a vertical direction of said blood collection reservoir,
comparing said output signals with a predetermined threshold value, and
determining the liquid level of the salvaged blood in said blood collection reservoir based on said comparing said output signals with said predetermined threshold value.

4. The autologous blood transfusion system as claimed in claim 1, wherein said processor is configured for individually adjusting detection parameters associated with said plurality of light emitters and said plurality of light receivers, said detection parameters including at least one of an output power of said light emitters, a gain of an amplifier used for amplifying output signals outputted by said plurality of light receivers and a threshold value used by said processor.

5. The autologous blood transfusion system as claimed in claim 1, wherein said processor is further configured for:
determining the liquid level of the salvaged blood in said blood collection reservoir using said varied detection parameter if a signal of a light receiver or amplifier associated with said varied detection parameter is not identified as a conspicuous signal in said identifying step when repeating said step of determining the liquid level of the salvaged blood in said blood collection reservoir using said varied detection parameter.

6. The autologous blood transfusion system as claimed in claim 1, wherein the processor is further configured for starting or controlling a washing process based on said liquid level determined by said processor upon reaching preset liquid levels in the blood collection reservoir, or for generating a warning message and outputting said warning message via an interface, if the liquid level determined by said processor indicates a complete or nearly complete depletion of the blood collection reservoir.

7. The autologous blood transfusion system as claimed in claim 1, wherein the output signal of the first of the at least two light receivers indicates a relatively high transmission and the output signal of the second of the at least two light receivers indicates a relatively low transmission, or the output signal of the first of the at least two light receivers indicates a relatively low transmission and the output signal of the second of the at least two light receivers indicates a relatively lower transmission.

8. The autologous blood transfusion system as claimed in claim 1, said conspicuous signal is associated with an abnormal transmission change between the output signals of three light receivers, the output signal of a first of the three light receivers being compared against the output signal of a second of the three light receivers and the output signal of the second of the three light receivers being compared against the output signal of a third of the three light receivers, and the three light receivers being directly adjacent.

9. The autologous blood transfusion system as claimed in claim 8, wherein the output signals of the first and third light receivers indicate a relatively high transmission and the output signal of the second light receiver indicates a relatively low transmission, or the output signals of the first and third light receivers indicate a relatively low transmission and the output signal of the second light receiver indicates a relatively lower transmission.

10. A method for determining a liquid level of salvaged blood in a blood collection reservoir of an autologous blood transfusion system, comprising a plurality of light emitters disposed on a first side of said blood collection reservoir at different height levels for emitting light and a plurality of light receivers disposed on a second side of said blood collection reservoir opposite to said first side for detecting light emitted by said light emitters and transmitted through said blood collection reservoir, said method comprising:
periodically activating said plurality of light emitters for emitting light;
detecting light transmitted through said blood collection reservoir using said plurality of light receivers;
determining the liquid level of salvaged blood in the blood collection reservoir based on output signals outputted by said plurality of light receivers;
identifying a conspicuous signal out of said output signals of said light receivers based on a comparison of output signals of at least two light receivers out of said plurality of light receivers, said conspicuous signal associated with an abnormal transmission change between the output signals of the at least two light receivers, the output signal of a first of the at least two light receivers being compared against the output signal of a second of the at least two light receivers and the first and second light receivers being directly adjacent;
varying a detection parameter of a light emitter and/or of a light receiver and/or of an amplifier associated with said conspicuous signal; and
repeating said step of determining the liquid level of the salvaged blood in said blood collection reservoir using said varied detection parameter.

11. The method as claimed in claim 10, wherein said light emitters are switched on and off individually in correspondence to a control signal to thereby emit light pulses, and wherein output signals outputted by light receivers that correspond to said light emitters are analyzed individually and in correspondence with said control signal.

12. The method as claimed in claim 10, further comprising:
reading-out output signals output by said light receivers sequentially along a vertical direction of said blood collection reservoir;
comparing said output signals with a predetermined threshold value; and
determining the liquid level of the salvaged blood in said blood collection reservoir based on said step of comparing said output signals with said predetermined threshold value.

13. The method as claimed in claim 10, further comprising:
individually adjusting detection parameters associated with said plurality of light emitters and said plurality of light receivers, said detection parameters including at least one of an output power of said light emitters, a gain of an amplifier used for amplifying output signals outputted by said plurality of light receivers and a threshold value used for determining the liquid level.

14. The method as claimed in claim 10, further comprising:
determining the liquid level of the salvaged blood in said blood collection reservoir using said varied detection parameter if a signal of a light receiver or amplifier associated with said varied detection parameter is not identified as a conspicuous signal in said identifying step when repeating said step of determining the liquid level of the salvaged blood in said blood collection reservoir using said varied detection parameter.

15. The method as claimed in claim 10, wherein a washing process is started or controlled based on said liquid level determined by said processor upon reaching preset liquid levels in the blood collection reservoir, or wherein a warning message is generated and output via an interface, if the liquid level determined by said processor indicates a complete or nearly complete depletion of blood collection reservoir.

16. The method as claimed in claim 10, wherein the output signal of the first of the at least two light receivers indicates a relatively high transmission and the output signal of the second of the at least two light receivers indicates a relatively low transmission, or the output signal of the first of the at least two light receivers indicates a relatively low transmission and the output signal of the second of the at least two light receivers indicates a relatively lower transmission.

17. The method as claimed in claim 10, wherein said conspicuous signal is associated with an abnormal transmission change between the output signals of three light receivers, the output signal of a first of the three light receivers being compared against the output signal of a second of the three light receivers and the output signal of the second of the three light receivers being compared against the output signal of a third of the three light receivers, and the three light receivers being directly adjacent.

18. The method as claimed in claim 17, wherein the output signals of the first and third light receivers indicate a relatively high transmission and the output signal of the second light receiver indicates a relatively low transmission, or the output signals of the first and third light receivers indicate a relatively low transmission and the output signal of the second light receiver indicates a relatively lower transmission.

* * * * *